United States Patent [19]

Purcell et al.

[11] 4,101,433
[45] Jul. 18, 1978

[54] COMPOSITION

[75] Inventors: Robert F. Purcell; James R. Selleck, Jr., both of Terre Haute, Ind.

[73] Assignee: IMC Chemical Group, Inc., Terre Haute, Ind.

[21] Appl. No.: 781,250

[22] Filed: Mar. 25, 1977

[51] Int. Cl.² ............................................. C10M 3/04
[52] U.S. Cl. ................................... 252/49.5; 252/49.3; 252/180; 424/248.4; 424/348
[58] Field of Search ..................... 252/49.3, 49.5, 180; 424/248.4, 348

[56] References Cited

U.S. PATENT DOCUMENTS

| | | | |
|---|---|---|---|
| 3,054,748 | 9/1962 | Hodge | 424/248.4 X |
| 3,054,749 | 9/1962 | Bennett et al. | 424/248.4 X |
| 3,192,163 | 6/1965 | Hodge | 424/248.4 X |
| 3,257,320 | 6/1966 | Hodge | 252/49.5 X |
| 3,647,703 | 3/1972 | Shema et al. | 424/248.4 X |
| 3,836,654 | 9/1974 | Hodge | 424/248.4 |
| 3,860,516 | 1/1975 | Shema et al. | 424/248.4 X |
| 3,860,517 | 1/1975 | Shema et al. | 424/248.4 |
| 3,897,554 | 7/1975 | Shema et al. | 424/248.4 |
| 3,932,654 | 1/1976 | Brandman | 252/49.5 X |

OTHER PUBLICATIONS

Chemical Abstracts, 50, 11656d (1956).
Chemical Abstracts, 47, 11663c (1953).
Chemical Abstracts, 54, 6872a (1959).
Chemical Abstracts, 54, 18660d (1960).

*Primary Examiner*—Helen M. S. Sneed
*Attorney, Agent, or Firm*—Robert H. Dewey; Howard E. Post

[57] ABSTRACT

A composition consisting essentially of tris(hydroxymethyl)nitromethane and about an equal part of a mixture consisting of 4-(2-nitrobutyl)morpholine and 4,4-(2-ethyl-2-nitromethylene)dimorpholine in a ratio of about 3.5:1 respectively. The composition is useful as an antimicrobial.

4 Claims, No Drawings

COMPOSITION

BACKGROUND OF THE INVENTION

This invention relates to a composition of antimicrobial agents. In a particular aspect this invention relates to an antimicrobial composition useful for controlling the growth of microorganisms.

One of the problems in metalworking industries is the susceptibility of metalworking fluids (which are emulsions of oil or chemical lubricants in water) to microbial attack. Were it not for this microbial contamination, the oil could be used for many months, but actually the microbial growth shortens the working life of the oil considerably. Microbial action may cause the emulsion to break and become acidic, thus causing corrosion problems. Some of the microbes may be pathogenic which can cause skin infections and other industrial health problems. In addition the microbial mycelia can clog pumps and valves, and often a foul odor develops. In a large installation, frequent replacement of metalworking fluids is costly.

Tris(hydroxymethyl)nitromethane has long been used for antimicrobial purposes, e.g. in metalworking fluids. Its effectiveness for this use was described by H. O. Wheeler and E. O. Bennett, *Applied Microbiology* 4, 122–126 (1956); and E. O. Bennett, *Soap and Chemical Specialties* 32, 47–49 (October 1956); 46–48 (November 1956). The product has been particularly useful in preserving aqueous media such as cutting oils, latex paint, recirculated cooling water, etc. However it lacks long term stability under some conditions of use and additional amounts must be added periodically in long term applications.

The mixture of 4-(2-nitrobutyl)morpholine and 4,4-(2-ethyl-2-nitrotrimethylene)dimorpholine has also been long known for its antimicrobial properties. It is available commercially as Bioban ® P-1487 from IMC Chemical Group, Inc. Hereinafter this mixture will be referred to as P-1487. P-1487 is a highly effective antimicrobial and is advantageous over tris(hydroxymethyl)nitromethane in that it is quite stable under use conditions. However it is expensive by comparison to the latter, which is quite low cost.

SUMMARY OF THE INVENTION

It is an object of this invention to provide an antimicrobial composition.

It is another object of this invention to provide an antimicrobial composition having particular utility in aqueous systems.

Other objects will be apparent to those skilled in the art from the description herein.

It is the discovery of this invention that tris(hydroxymethyl)nitromethane and P-1487 form a highly effective antimicrobial combination in about a 1:1 by weight mixture. The combination is effective against a broad spectrum of bacteria and fungi.

DETAILED DISCUSSION

The combination of the present invention is effective for controlling the growth of a wide variety of microorganisms. Surprisingly, the combination when used in petroleum based cutting oils is effective over a long period of time. The combination is generally effective to combat the growth of microorganisms at a concentration of at least about 250 ppm. However, depending on the vigor of the organisms, the length of time during which growth should be suppressed, etc., concentrations of about 1000 ppm or even up to 1500 or 2000 ppm may be preferred.

The tris(hydroxymethyl)nitromethane (commonly referred to as TN) used in the combination of this invention is commercially available both in crystalline form and as a 50% aqueous solution. Either is suitable for the practice of this invention. TN is formed by the condensation of 3 moles of formaldehyde with 1 mole of nitromethane as is known in the art.

P-1487 is also commercially available and the commercial grade is suitable for the practice of the invention. P-1487 is formed by the reaction of 1-nitropropane with morpholine and formaldehyde in a mole ratio of 1.0:3:1.3. The general reaction to form nitro amines is described by M. Senkus and H. G. Johnson, J. Am. Chem. Soc. 68, 10–14 (1946). Two products are formed in this reaction, 4-(2-nitrobutyl)morpholine, 70%, and 4,4'-(2-ethyl-2-nitrotrimethylene)dimorpholine, 20%, (i.e. in a ratio of about 3.5:1) with about 10% inactive ingredients.

The preferred combination for the practice of this invention is TN and P-1487 in a ratio of about 1:1. However, it is not intended that the practice of this invention be narrowly limited to this precise composition. A composition of 1.3:0.7 will give excellent results and will be regarded as the practical equivalent of the 1:1 mixture. Accordingly, it is contemplated that the composition may vary from 0.7–1.3:1.3–0.7 respectively, of TN and P-1487 providing the following composition:

| | Compositon of TN and P-1487 | | |
|---|---|---|---|
| Ratio, by weight | 0.7:1.3 | 1:1 | 1.3:0.7 |
| Tris(hydroxymethyl)-nitromethane | 35.0% | 50.0% | 65.0% |
| 4-(2-Nitrobutyl)morpholine | 45.5 | 35.0 | 24.5 |
| 4,4'-(2-Ethyl-2-nitrotrimethylene)dimorpholine | 13.0 | 10.0 | 7.0 |
| Inactive ingredients | 6.5 | 5.0 | 3.5 |

The combination is preferably employed in neutral or slightly alkaline solutions, i.e. at a pH of about 7.0 to 8.5. Loss of effectiveness of P-1487 may occur at pH below about 6. The preferred pH range is often provided by the use of anionic surfactants or other additives. If necessary, a mildly alkaline substance, many of which are known, e.g. sodium carbonate may be added to the combination or substrate at the time of use.

The method of controlling microorganisms of this invention comprises application of the antimicrobial combination to a substratum infested with the microorganisms to be controlled or to a substratum to be protected from infestation with the microorganisms. The term substratum as used herein is intended to mean the environment or medium upon which an organism grows and includes both animate and inanimate matter, such as animal and vegetable, living or dead, and the soil. The terms microbe and microorganism as used herein are intended to include bacteria and fungi. The term antimicrobial as used herein is intended to include the terms bactericidal, bacteriostatic, fungicidal and fungistatic. No attempt has been made to determine if the products actually cause the death of the organism or merely prevent their growth. The combination is especially useful in cutting oils for metalworking, latex paints, and recirculated cooling water.

The antimicrobial combination of this invention is preferably supplied to the microorganisms or to the environment inhabited by them in the form of emulsions or suspensions. Tris(hydroxymethyl)nitromethane is very soluble in water as well as in many organic solvents. P-1487 is poorly soluble in water, but is soluble in most organic solvents. Emulsions or suspensions are prepared by dispersing the combination of this invention in water with the aid of a surface active agent. The combination can be emulsified directly or it can first be dissolved in an organic solvent and then emulsified. They can also be added separately, or first mixed and then added together.

The term "surface active agent" includes the various "emulsifying agents," "dispersing agents," "wetting agents" and "spreading agents" that can be mixed with the combination of this invention in order to obtain a dispersion of the combination in water. These surface active agents include the well-known anionic, cationic, or non-ionic surface active agents. In general, the water-soluble anionic surface active agents are preferred.

The preferred surface active agents which can be employed in preparing the emulsifiable, wettable or dispersible compositions of this invention include the anionic and non-ionic surface active agents. The preferred anionic surface active agents are the well-known water-soluble polyoxyethylene derivatives of the mono-higher fatty acid esters of hexitol anhydrides such as mannitan or sorbitan.

In controlling the growth of microorganisms the combination of this invention is supplied to the organisms or to their environment in a lethal or toxic amount. This can be done by dispersing the combination or a composition containing it, in, on or over an environment or substratum infested with, or to be protected from, the microorganisms. The combination or a mixture containing it can be dispersed in any conventional method which permits contact between the organisms and the antimicrobial agents of this invention. It is contemplated that the aqueous system to be protected contains the combination added by the manufacturer at the time of manufacture or preparation. Alternatively, the combination can be prepackaged and the proper amount added ad libitum. Or the components can be added separately at the time of use. Also, one component can be added at one time and the other at a later time. A preferred method is to incorporate the P-1487 in the system to be protected at the time of manufacture or preparation and to add the tris(hydroxymethyl)nitromethane at the time of use.

The term dispersed as used herein is intended to include true solutions, colloidal suspension and emulsions. It is not intended that the term dispersions be limited to any particular particle size or method of suspension.

The invention will be better understood with reference to the following examples. It is understood that the examples are intended to be illustrative only and it is not intended that the invention be limited thereby.

EXAMPLE 1

The antimicrobial properties for P-1487 and TN were determined by the tube dilution method. Media for the bacterial cultures was trypticase soya broth at pH 7.3 prepared as known in the art, and the media for the fungi was Sabouraud broth at pH 5.6, also prepared as known in the art. The inoculum was standardized by the pour plate method for a total viable organism count. The amount of the inoculum per tube was 5 ml at a population of $10^5$ organisms per ml.

The results, expressed as inhibition endpoints in parts per million show that at a 1:1 ratio the combination is more active against many microorganisms than either component alone. It was tested for anti-bacterial and anti-fungal activity against nine bacteria (4 Gram positive and 5 Gram negative) and eight fungi (6 molds and 2 yeasts). The results are listed in the table. They are reported as minimum inhibitory concentration, which is the range between the highest concentration which permits growth and the lowest concentration which prevents growth. They increase exponentially. Because of uncontrollable variables, such as the vigor of the organism, the data are reproducible to about plus or minus one range.

Table 1

| Organism | Minimum Inhibitory Concentrations, ppm | | |
|---|---|---|---|
| | 100% P-1487 | 50% TN 50% P-1487 | 100% TN |
| BACTERIA | | | |
| Bacillus subtilis | 125–250 | 125–250 | 125–250 |
| Staphylococcus aureus | 125–250 | 65–125 | 65–125 |
| Streptococcus faecalis | 250–500 | 125–250 | 250–500 |
| Sarcina lutea | 125–250 | 125–250 | 250–500 |
| Escherichia coli | 125–250 | 125–250 | 500–1000 |
| Aerobacter aerogenes | 125–250 | 65–125 | 500–1000 |
| Pseudomonas aeruginosa | 1000–2000 | 1000–2000 | 500–1000 |
| Salmonella typhii | 65–125 | 250–500 | 65–125 |
| Desulfovibrio aestaurii | <33 | 32–65 | 125–250 |
| FUNGI | | | |
| Cladosporium herbarum | 125–250 | 250–500 | >2000 |
| Cephalosporium species | <33 | 32–65 | — |
| Trichophyton mentagrophytes | 33–65 | 32–65 | 250–500 |
| Aspergillus niger | 65–125 | 250–500 | >2000 |
| Aureobasidium pullulans | <33 | 32–65 | >2000 |
| Fusarium moniliforme | <33 | 32–65 | >2000 |
| Saccharomyces cerevisiae | <33 | 65–125 | 1000–2000 |
| Candida albicans | <33 | 125–250 | >2000 |

EXAMPLE 2

A sample of a petroleum-based cutting oil emulsion was diluted 1:40 with water and 500 ml aliquots of the emulsion were used for long-term tests. The cutting oil used was Texaco 591 marketed by Texaco Oil Co.

To three samples of the diluted emulsion were added Bioban P-1487 ® at a concentration of 500, 750 and 1000 ppm respectively. To two additional samples were added TN as the 50% concentrate to provide 1500 and 2000 ppm TN respectively. To two more samples were added a 1:1 mixture of TN and P-1487 to provide a concentration of 250 ppm and 500 ppm respectively. One sample was used as an untreated control. To each sample was added 5 g of 40-mesh iron filings to simulate metal chips that would fall into the fluids in actual use.

A mixed bacterial culture having an overall population level of at least $10^8$ organisms per ml was prepared from equal population levels of the following organisms:
Pseudomonas aeruginosa
Escherichia coli
Aerobacter aerogenes
Salmonella typhii
Staphylococcus aureus
Streptococcus faecalis
Proteus vulgaris
Desulfovibrio desulfuricans
Two mixed populations isolated from a contaminated fluid.

To each of the above samples there was added 5 ml of the bacterial culture.

Similarly a mixed fungal culture having an overall population level of at least $10^5$ organisms per ml was prepared from equal population levels of the following organisms:
- Fusarium moniliforme
- Trichophyton mentagrophytes
- Cephalosporum species
- Cladosporium herbarum
- Penicillium velutinum
- Aspergillis niger
- Aureobasidium pullulans
- Candida albicans (yeast).

To each of the above samples was added 5 ml of the fungal culture.

The samples were kept at ambient room temperature for the duration of the testing and aerated with sterile air bubbled through them constantly for five days and shut down on the weekend to simulate use conditions.

The samples were streaked on TSA petri plates for the determination of bacterial growth at 24 hours, 48 hours, 72 hours, and one week post-inoculation. They were also streaked on SDA petri plates to check for fungal growth at one week post-inoculation. The agar plates were incubated at 30° C for 48 hours for the bacteria and for ten days for the fungi before being evaluated. After the one week post-inoculation streaking, each sample was reinoculated with the same organism population levels again and the petri plate streaking procedure was repeated. This was done for six weeks (minimum) to twelve weeks (maximum) if failure did not occur otherwise.

Organism growth was evaluated on a scale of 0 to 4 - zero being no visible growth, 1 being 1–10 colonies per agar plate, 2 being 11–25 colonies, 3 being 26–40 colonies, and 4 being over forty colonies. In order for a sample to pass it must have diminished the population level to 10 or less colonies in less than 48 hours. If it took between 48 and 72 hours to reduce the organism population, or if the population was only reduced to between 11 and 25 colonies, these samples were considered borderline protection. Everything else was failure. Sterility is not considered a prerequisite to the integrity of these fluids. It has been shown that as long as the population level of microorganisms in metalworking fluids is kept below 100,000 per ml, these fluids are still functional. Random pour plate counts were made on samples considered failures and in every case the bacterial populations were in excess of $10^5$ per ml. Elimination of the vast majority of microorganisms and a stasis effect on the few remaining inactive cells have been shown to protect the product as well as does complete sterility. In addition to the microbiological checking of the fluids, visual interpretations were also made. Emulsion breakdown, slime build-up, and large mold growths in or on top of the fluids were also criteria used to evaluate the usefulness of the fluid. The results obtained are given in Table 2

Table 2

|  | Weeks Protected | |
|---|---|---|
|  | Bacteria | Molds |
| P-1487 at 1000 ppm | >16 | >16 |
| TN at 1500 ppm | 6 | 5 |
| P-1487 (500 ppm) + TN (500 ppm) | 7 | 7 |
| P-1487 at 500 ppm | 5 | 4 |
| P-1487 (250 ppm) + TN (250 ppm) | 6 | 6 |

These data show that the combination at a total concentration of 1000 ppm is superior to TN at 1500 ppm. Also, surprisingly and unexpectedly, 500 ppm of the mixture give results superior to 500 ppm of the P-1487 alone and nearly as good as 1000 ppm of the combination.

We claim:

1. A composition consisting essentially of tris(hydroxymethyl)nitromethane and P-1487 in a weight ratio of from about 0.7:1.3 of tris(hydroxymethyl)nitromethane to about 1.3:0.7 of P-1487, the latter consisting essentially of 4-(2-nitrobutyl)morpholine and 4,4'-(2-ethyl-2-nitrotrimethylene)dimorpholine in a ratio of 3.5:1, respectively.

2. A method of controlling the growth of bacteria and fungi by applying to them or the environment inhabited by them the composition of claim 1 in an amount sufficient to provide a total concentration of from about 500 to about 1500 ppm.

3. A petroleum-based cutting oil emulsion protected from undue contamination by bacteria and fungi by an antimicrobial agent consisting essentially of the composition of claim 1.

4. A method of controlling the growth of bacteria and fungi in a petroleum-based cutting oil emulsion comprising the step of incorporating in the emulsion an amount of the composition of claim 1 sufficient to provide a concentration of from about 500 to 1500 ppm.

* * * * *